（12）United States Patent
Hassouneh et al.

(10) Patent No.: US 10,330,574 B2
(45) Date of Patent: *Jun. 25, 2019

(54) BIOLOGICAL FLUIDS CONCENTRATION ASSEMBLY

(71) Applicant: Alliance Partners LLC, San Antonio, TX (US)

(72) Inventors: Emad Hassouneh, San Antonio, TX (US); Logan White, Garfield Heights, OH (US); Matt Schmidt, Avon Lake, OH (US); Andrew Enke, San Antonio, TX (US); Frank Morris, Austin, TX (US)

(73) Assignee: ALLIANCE PARTNERS, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/798,034

(22) Filed: Oct. 30, 2017

(65) Prior Publication Data

US 2018/0120206 A1    May 3, 2018

Related U.S. Application Data

(62) Division of application No. 14/226,248, filed on Mar. 26, 2014, now Pat. No. 9,804,070.

(Continued)

(51) Int. Cl.
  *G01N 1/40*    (2006.01)
  *G01N 35/10*   (2006.01)
  (Continued)

(52) U.S. Cl.
  CPC .......... *G01N 1/4077* (2013.01); *B01L 3/5021* (2013.01); *A61M 1/0009* (2013.01);
  (Continued)

(58) Field of Classification Search
  CPC .... B01L 2400/0478; B01L 2400/0633; A61M 1/0009; A61M 1/0068
  See application file for complete search history.

(56) References Cited

U.S. PATENT DOCUMENTS 3,512,651 A    5/1970   Laval, Jr.
3,706,306 A    12/1972  Berger et al.
(Continued)

*Primary Examiner* — Lyle Alexander
*Assistant Examiner* — Bryan Kilpatrick
(74) *Attorney, Agent, or Firm* — Dickinson Wright PLLC; Ross Spencer Garsson

(57) ABSTRACT

A biological fluids concentration device, including a tube-in-tube assembly, is disclosed. The tube-in-tube assembly receives biologic fluids and may then be placed in the bucket of a centrifuge and spun to separate out the components of the biological fluid by their various densities. For example, whole blood may be centrifuged in the tube-in-tube assembly for separating into plasma, red blood cell component, and a buffy coat. A piston slideably and sealingly engages an inner tube of the tube-in-tube assembly, the inner tube fitting within an outer tube. A lid is designed to engage the top of the outer tube, which lid has an opening therein for receipt of a plunger. The plunger is adapted to move up and down with respect to the lid and the tubes, so as to sealingly, in a down position, and unsealingly, in an open position, engage the top of the inner tube of the tube-in-tube assembly.

12 Claims, 14 Drawing Sheets

Related U.S. Application Data

(60) Provisional application No. 61/880,485, filed on Sep. 20, 2013, provisional application No. 61/805,346, filed on Mar. 26, 2013.

(51) Int. Cl.
    *A61M 1/00*     (2006.01)
    *A61M 1/36*     (2006.01)
    *B01L 3/00*     (2006.01)

(52) U.S. Cl.
    CPC ......... *A61M 1/0068* (2014.02); *A61M 1/3693* (2013.01); *B01L 2300/042* (2013.01); *B01L 2300/046* (2013.01); *B01L 2300/049* (2013.01); *B01L 2300/0854* (2013.01); *B01L 2300/0864* (2013.01); *B01L 2400/0478* (2013.01); *B01L 2400/0633* (2013.01); *G01N 35/10* (2013.01)

(56) References Cited

U.S. PATENT DOCUMENTS

| | | |
|---|---|---|
| 3,969,250 A | 7/1976 | Farr |
| 4,142,668 A | 3/1979 | Lee |
| 4,488,048 A | 12/1984 | Bienek et al. |
| 5,100,372 A | 3/1992 | Headley |
| 5,165,572 A * | 11/1992 | Bath .................... B65D 47/248 206/204 |
| 5,707,331 A | 1/1998 | Wells et al. |
| 6,277,060 B1 | 8/2001 | Neumann |
| 6,835,353 B2 | 12/2004 | Smith et al. |
| 7,179,391 B2 | 2/2007 | Leach et al. |
| 7,829,022 B1 | 11/2010 | Lich |
| 8,177,072 B2 | 5/2012 | Chapman et al. |
| 8,251,990 B2 | 8/2012 | Kaouk |
| 9,804,070 B2 * | 10/2017 | Hassouneh .......... G01N 1/4077 |
| 2002/0016244 A1 | 2/2002 | Unger et al. |
| 2004/0067162 A1 | 4/2004 | Haubert et al. |
| 2009/0031790 A1 | 2/2009 | Guo et al. |
| 2013/0045852 A1 | 2/2013 | Chapman et al. |

\* cited by examiner

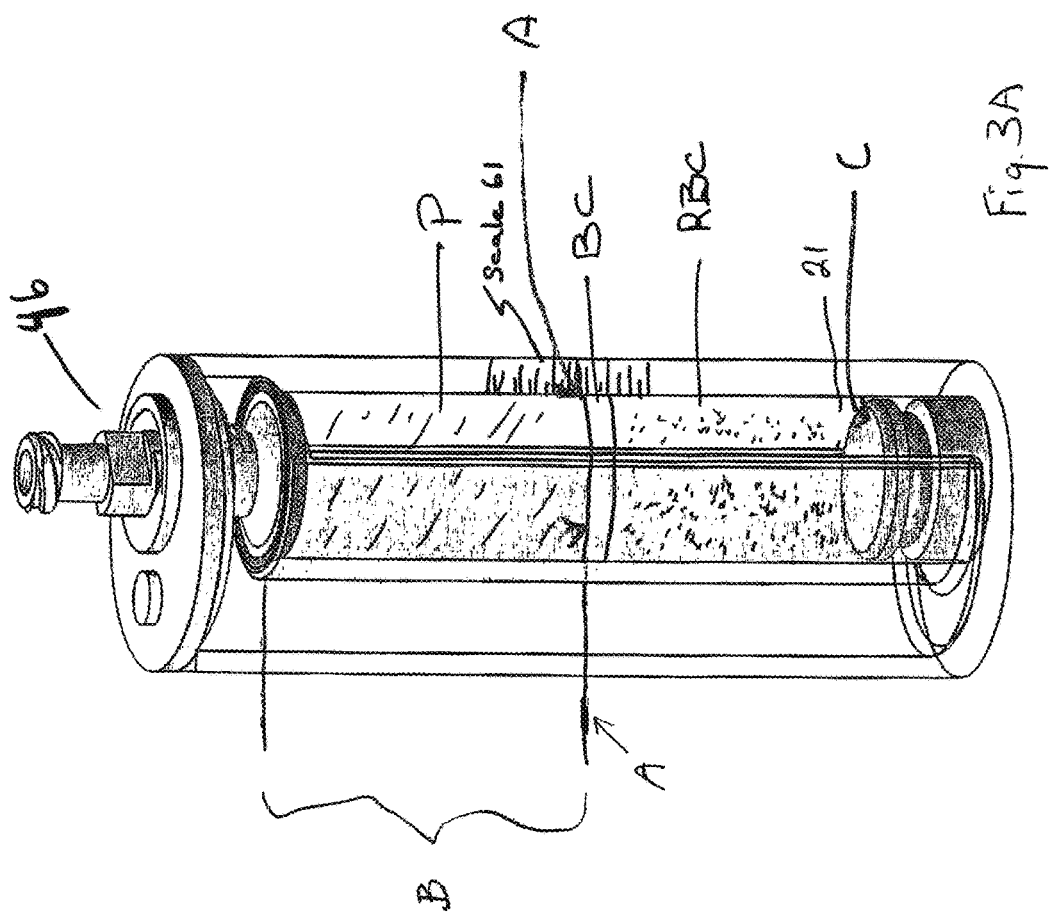

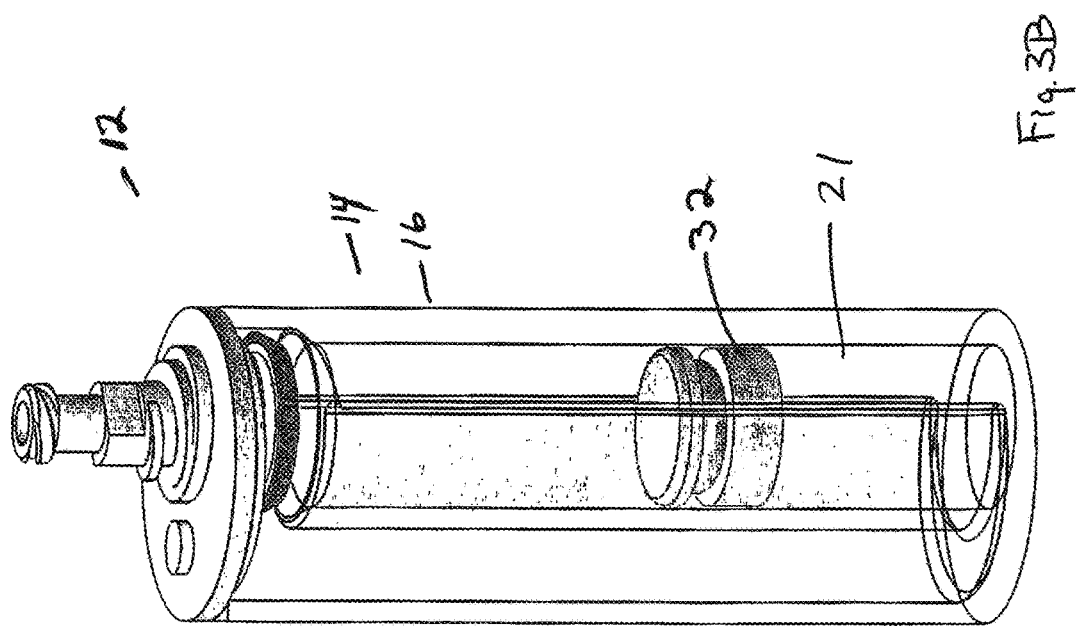

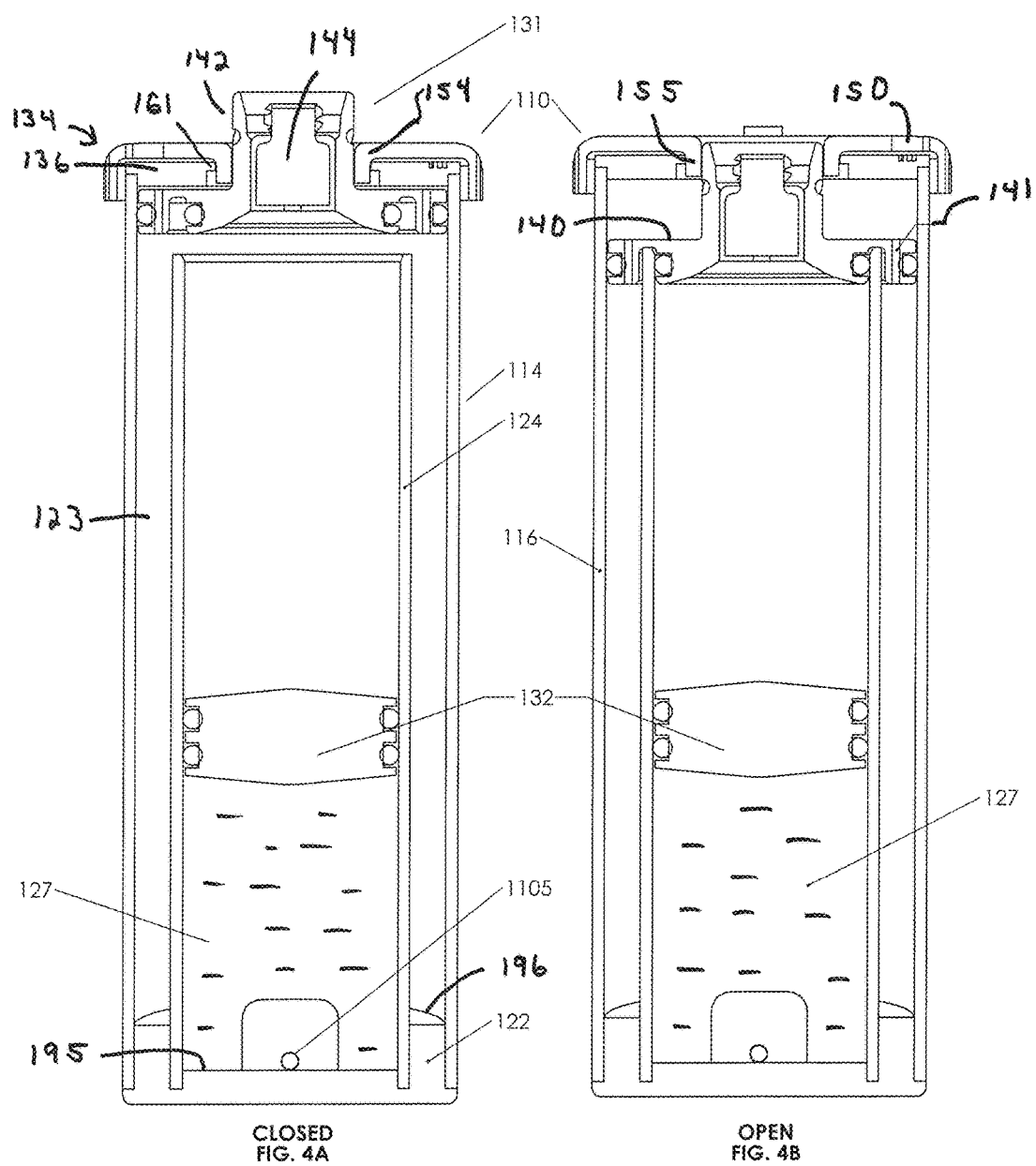

OPEN

CLOSED

BIOLOGICAL FLUIDS CONCENTRATION ASSEMBLY

RELATED APPLICATIONS

This application is a divisional application of and claims priority and benefit to U.S. patent application Ser. No. 14/226,248, filed on Mar. 26, 2014, which is a utility patent application claiming priority from and the benefit of U.S. Provisional Patent Application No. 61/805,346, filed Mar. 26, 2013; and U.S. Provisional Patent Application No. 61/880,485, filed Sep. 20, 2013. All of these applications are incorporated herein by reference.

FIELD OF THE INVENTION

Concentration assemblies, namely, concentration assemblies adapted to concentrate biological fluids under centrifuge.

BACKGROUND

Biological fluids, such as blood, bone marrow aspirate, and the like, are often subject to centrifuge so as to separate them by density into their separate components. For example, blood, when centrifuged, will separate into red blood cell components (denser) and a plasma component (less dense) with a small percentage of buffy coat between. Bone marrow aspirate, when centrifuged, will typically separate into a red blood cell (platelet) component, a plasma component, and a buffy coat component comprising stem cells or undifferentiated cells.

SUMMARY OF THE INVENTION

Applicant provides a fluid concentration assembly that has a "cup within a cup," wherein the inner cup is adapted to receive a biological fluid and has a gap between it and the outer cup. The concentration assembly is adapted to be received into a centrifuge machine and subject to centrifugation. Following centrifugation, a piston in the inner cup pushes up from below on the separated contents to force spillover of the less dense liquid into the gap, until the desired component is at the top of the inner cup. At this point, the open top of the inner cup may be sealed with a moveable sealing member and the piston driven further upward into a collection vessel engaging the sealing member.

In certain embodiments, the biological fluids concentration assembly includes a tube in tube assembly having a cylindrical outer tube and a cylindrical inner, smaller diameter, tube both having open tops and open bottoms. The open top of the inner tube is located below the top of the larger (outer) tube. A base engages the outer and inner tubes at the bottom ends thereof, the base allowing fluid communication between the exterior of the tube assembly and the interior of the inner tube. A piston is provided for slidably and fluid sealingly engaging the inner walls of the inner tube above the base and below the top. A lid is provided for sealing tightly to the open top of the outer tube, the lid having a central opening or bore. In certain implementations, the lid also has anti-rotation tabs attached to the surface thereof. A plunger assembly engages the tube in tube assembly and includes a plunger and an external cap with inner rim walls defining a central bore. The inner walls may also have projecting bosses. The cap includes walls configured for rotatable engagement with the lid. The plunger has a base and a neck engaging the base, the plunger having a fluid channel therethrough. The neck has drive tracks that engage the bosses of the external cap. Rotation of the external cap moves the plunger from an open position wherein the lower surface of the base is off the open top of the inner tube to a closed or down position, wherein the lower surface of the base engages the open top of the inner tube so as to fluidly seal it.

The plunger includes a channel for fluid communication through the plunger from the top surface of the plunger to the bottom surface. The channel bottom opening is positioned over the inner tube. Thus, a fluid containing device (e.g., a syringe) containing a fluid may be coupled to the top of the neck of the plunger (usually in the up or open position), as by threadable engagement, and a fluid, such as a biological fluid needing centrifuge separation, may be urged through the plunger into the inner tube. The plunger can then be moved to a closed position where the base of the plunger seals the top of the inner tube (thus avoiding spillage), and the entire assembly may be inserted into a centrifuge and spun. Following centrifuging, the piston in the inner tube may be driven upward. If the piston is driven upward and the plunger is in the up or open position, the less dense fluid (typically plasma) will be the first to spill over into a gap between the inner tube and the outer tube. When the less dense fluid is all or mostly all spilled over into the gap, the target of collection (usually the buffy coat) will be at the top of the inner tube. The user may then move the plunger to a closed position, as by rotating the external cap. In the closed position, the plunger is fluidly sealed against the upper perimeter of the inner tube. Further urging upward of the piston will force the fluid in the inner tube (the centrifuged separated fluid) into an empty fluid collection device (e.g., a syringe) attached to the neck of the plunger.

In particular implementations, the tube in tube elements are made of a clear material, such as clear plastic. Thus, the user may observe as the piston is urged upward and the centrifuged fluid is urged into a spillover situation or into a syringe engaging the top of the neck and selectively choose when to cease urging the piston upward, for example, when a buffy coat is substantially received within the fluid receiving syringe. The selected liquid may be collected in the syringe after the plunger is moved to the down position, by either suction from the syringe or pushing up on the piston.

In some embodiments, a fluid, such as a saline solution, may be driven into or withdrawn from the portion of the inner tube that is beneath the piston by use of a syringe that may be threaded into a fluid device interface engaging the base of the tube in the tube assembly. That is to say, the base of the tube in tube assembly provides for fluid communication into the inner tube and also seals the bottom of the inner tube.

BRIEF DESCRIPTION OF THE DRAWINGS

FIG. 3A shows a post-centrifuge pre-withdrawal condition of Applicants collection cup.

FIG. 3B illustrates the spillover step, wherein the less dense plasma has been urged up and out of the inner container into the larger cup.

FIGS. 4A and 4B are cross-sectional views of the second biological fluid concentration assembly in an open and a closed position, respectively.

DETAILED DESCRIPTION OF THE PREFERRED EMBODIMENT

Figure 1:
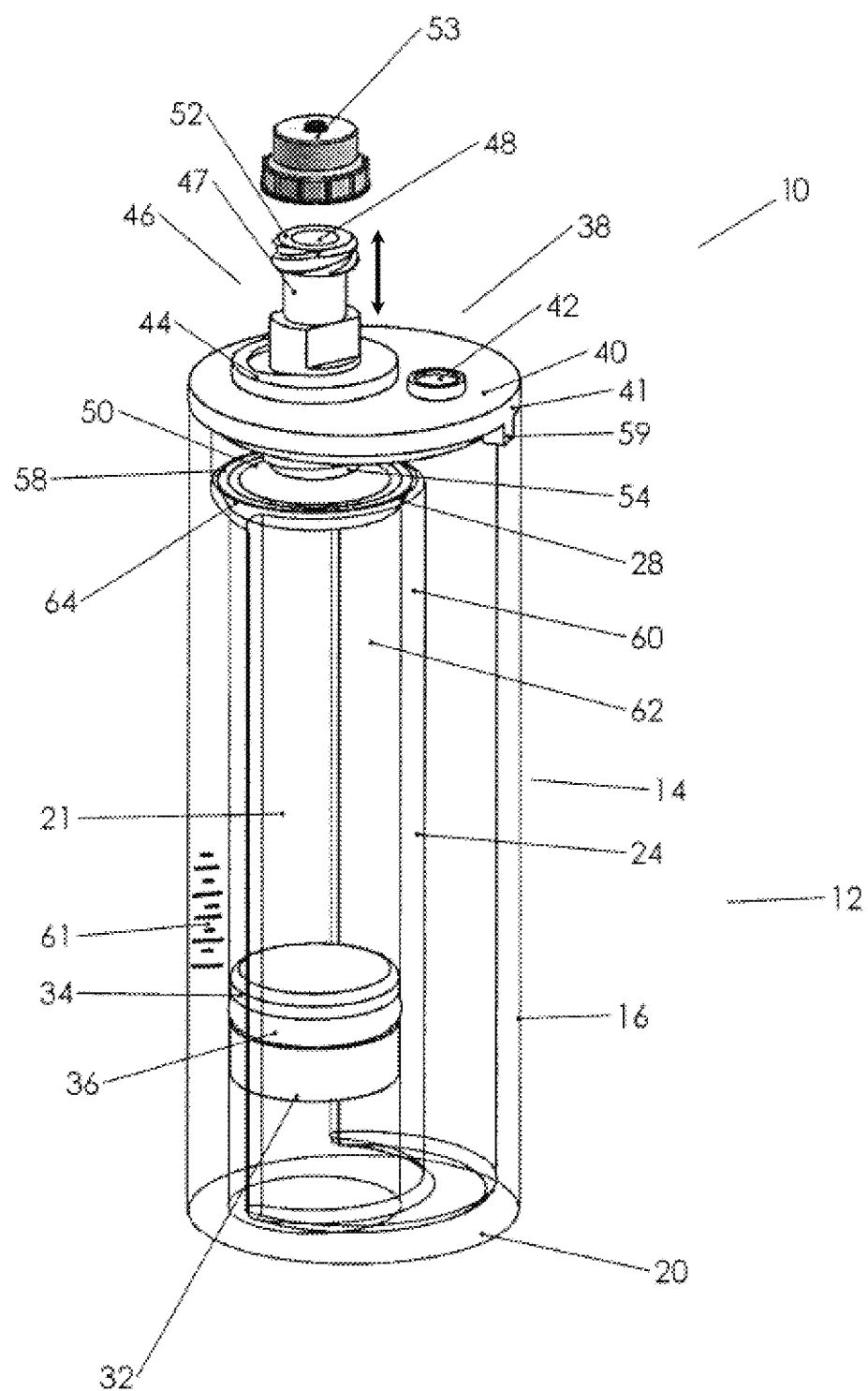
FIG. 1 is a perspective view of an example biological fluids concentration assembly.

A first embodiment of a fluid concentration assembly 10 (FIGS. 1A-3C) includes a container-in-container assembly 12 having an outer container 14 with a cup or tube interior and an inner container 24 with a tube interior with an open bottom 30 and open top 28, the top within the interior of outer container 14. Piston 32 is adapted to be slideably and sealingly received within open bottom 30 of inner container 24 as illustrated and typically includes a perimeter groove 34 with an elastomeric O-ring 36 (or other suitable sealing member) on a circumference thereof for fluid sealing against the inner walls of inner container 24. A lid 38 is seen to engage an open top 18 of outer container 14. Outer container 14 is typically cylindrical and is dimensioned to receive inner container 24 there within, such that the inner container has a smaller diameter than the outer container 14, and has an open top below the open top of outer container 14. Outer container 14 has side walls 16 and an upper perimeter 19 defining open top 18. A bottom wall 20 partly closes the bottom of outer container 14, but has an inner perimeter 30a that defines an open bottom area 30 (see FIG. 1A).

In the illustrated implementation, the outer wall of inner container 24 touches, and may be integral with, the inner wall of outer container 14. Thus, inner container 24 and outer container 14 share a portion of a wall in common. In other implementations, the outer wall of inner container 24 may not touch the inner wall of outer container 14.

Turning to lid 38, lid 38 is seen to have a cylindrical cover 40 dimensioned to receivably and removably engage open top 18 in a snug tight manner. Cover 40 is seen to have a rim 41 that is about the same diameter as open top 18. A port 42 is provided through cover 40 to provide gaseous communication between the interior of container 14 and the exterior thereof. Port 42 may be closed by a plug 45. Cover 40 also includes a bore 39 defined by threaded walls 44, which are adapted to receive a threaded section 54 of a moveable plunger 46. The engagement of threaded section 54 and threaded walls 44 of cover 40 allows the longitudinal movement of plunger 46 inward or outward as shown by the arrows adjacent thereto in FIG. 1.

Figure 1A:
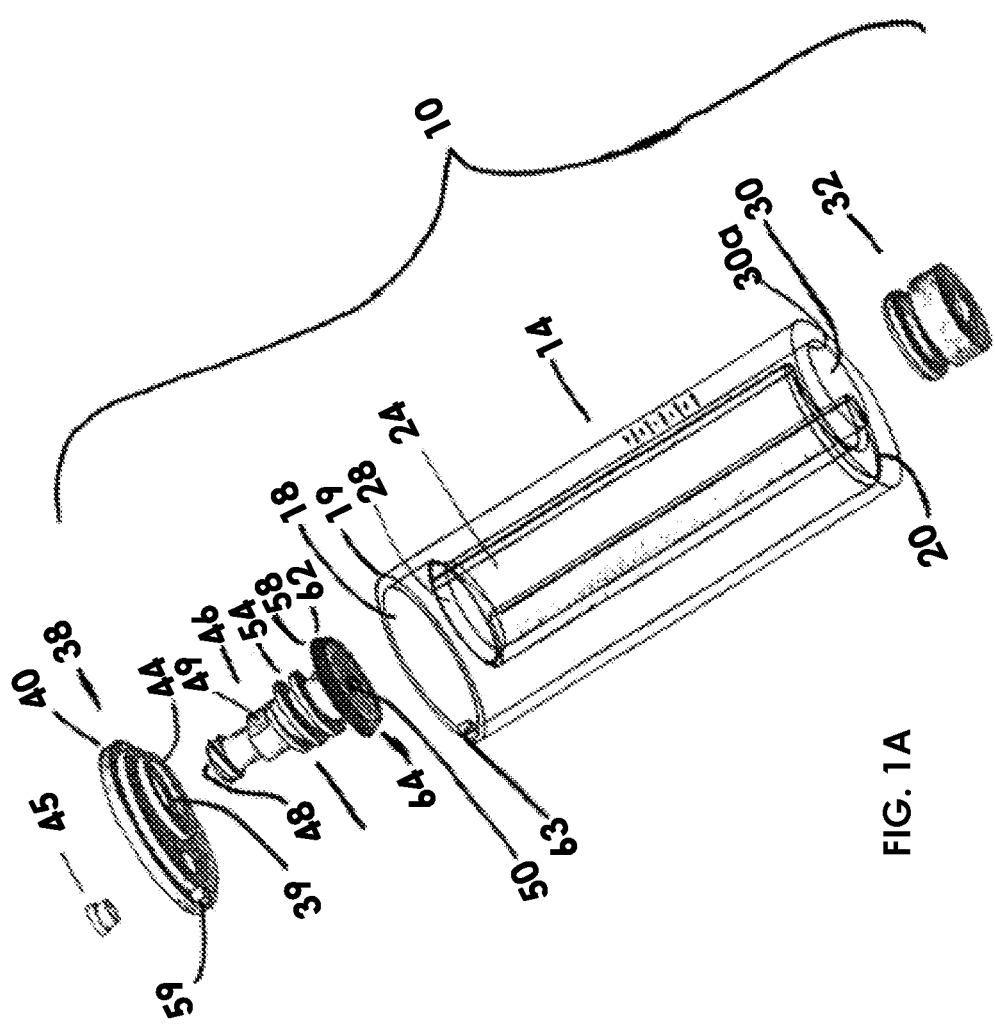
FIG. 1A is a perspective exploded view of the biological fluids concentration assembly.
Figure 2:
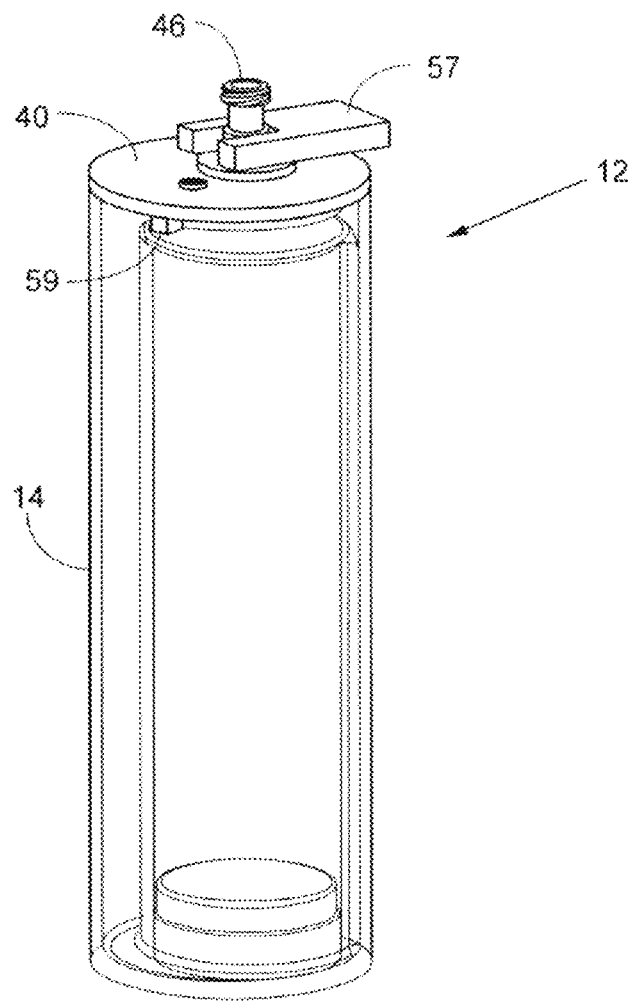
FIG. 2 is a perspective view illustrating the use of a tool with the assembly.

In FIGS. 1 and 1A, plunger 46 includes a neck or body 47 that has an exterior open end 48, which includes a threaded section 52 for receipt of a cap 53 threadably thereon, which will substantially seal exterior opening 48. Body 47 is seen to have an exterior portion, an interior portion, and an interior open end 50. Body 47 has an inner channel, which provides fluid communication between exterior open end 48 and interior open end 50, which interior open end opens above the interior of the inner container 24 and which exterior open end 48 is exterior of the cover. Interior open end 50 includes a base or cone-shape member 58 that extends outward from interior open end 50 and is positioned directly over open top 28 of inner container 24. Member 58 has an open apex 60, which is sealed to a perimeter interior open end 50. Member 58 is seen to have an outer perimeter 62 adapted, for example, being cup-shaped or arcuate shaped, so as to receive sealing member 64 (herein depicted as a resilient O-ring, although it could be another elastomeric sealing member). The perimeter 62 and the sealing member are dimensioned and the moveable plunger 46 is dimensioned relative to cover 40, such that the longitudinal movement of plunger 46 may seat or unseat sealing member 64 against open top 28 of inner container 24. Plunger 46 is also seen to have tool engaging walls 49, such that a tool 57 (see FIG. 2) may engage the tool engaging walls of the plunger, so as to rotate plunger 46 with respect to (fixed) cover 40 so as to advance sealing member 64 from an open position (open top 28 unobstructed) to a closed position (sealing member 64 against open top 28, such that it is now closed). Plunger 46 may also be retracted so as to open open top 28. Cover 40 is seen to have an alignment boss 59, and open top 18 has a rim cutout 63, so as to properly align plunger 46 such that the perimeter 62 is directly above open top 28 and, further, to prevent the rotation of cover 40 when tool 57 is used to rotate moveable plunger 46.

Figure 3:
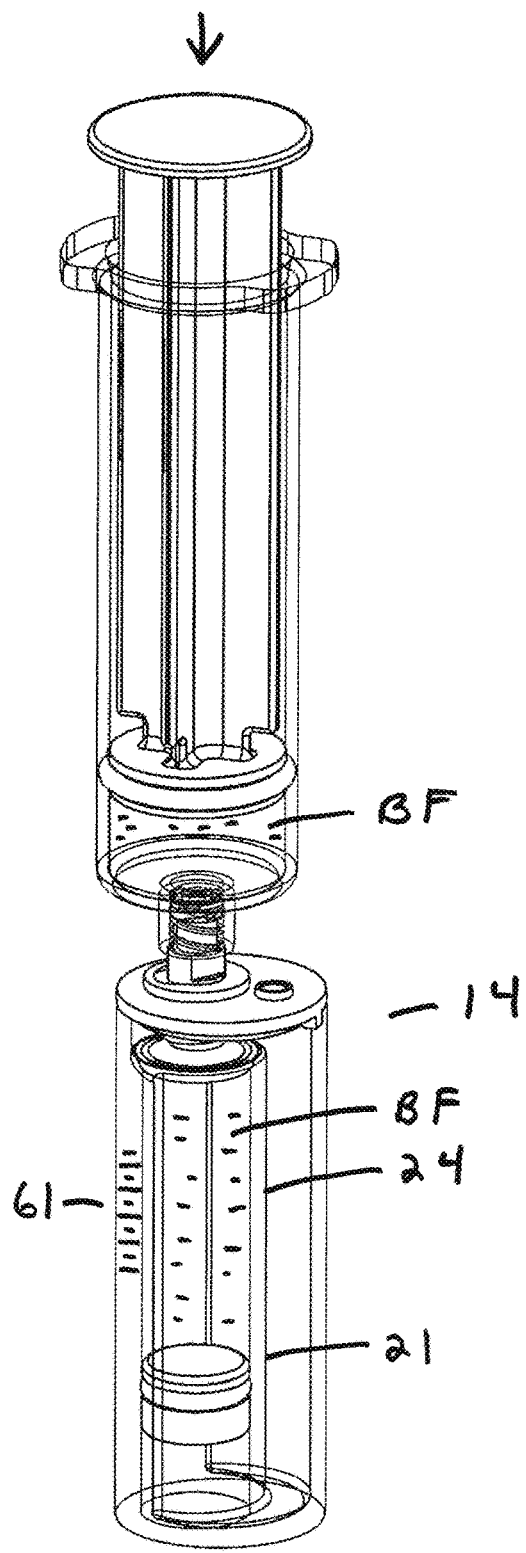
FIG. 3 illustrates in perspective view the manner in which a syringe with a biological fluid therein may engage Applicant's biological assembly to substantially fill an inner container.

In operation, briefly, the physician will collect a biological fluid BF from a patient and then physically engage a syringe or other biological fluid collection device to the top of the concentration assembly as indicated in FIG. 3. The plunger 46 may be in an open or closed position at this point. The physician will then push the plunger or otherwise cause the biological fluid BF to flow through the moveable plunger into the inner container. Piston 32 will be at or near the bottom of the inner container. Typically, the inner container 24 will be substantially filled with biological fluid BF (see FIG. 3).

The syringe is then removed, and the assembly is taken to a centrifuge and spun. In some implementations, plunger 46 may be moved to a closed position before centrifuging. During spinning, the fluids comprising the biological fluids will separate out according to their densities (see FIG. 3A). FIG. 3A shows a biological fluid (here, bone marrow aspirate) with three components: red blood cell RBC (most dense), plasma P (least dense), and buffy coat BC (typically comprising undifferentiated or stem cells), the buffy coat being intermediate between the plasma and the red blood cells. FIGS. 3A and 1 illustrate that there may be a scale 61 with numerals adjacent thereto along a common wall 21, for example, which common wall 21 is a side wall that is common to both the inner container 24 and outer container 14.

Turning to FIG. 3A, the user may note the location of the upper buffy coat/lower plasma border A as it lies adjacent indicia of the scale 61. The port 47 may then be opened and the plunger 46 raise, if it is not already up. Following raising of plunger 46 to the open position (see FIG. 3B), piston 32 may be urged upward by user manipulation (e.g., insertion of a digit), forcing spillover of the plasma at the open top 28 of inner container 24 into the gap. Movement is continued until the upper surface of the piston has traveled the "B" distance as measured up from "C" (start position of the upper surface of the piston). The P/BC boundary should then be adjacent open top 28. At this point, most, if not all, of plasma P has spilled over open top 28 and lies in the gap between the inner and outer containers. When such a level is reached, plunger 46 may be lowered and a collection device for collection of the non-plasma portion (typically buffy coat) or whatever selected portion is left in the inner container may be achieved.

In one aspect of Applicant's device, when a collection device is threaded to exterior open end 48 for receipt of selected fluid therein, urging upward of the piston will force, or at least assist, the selected fluid up into the collection device. This is not the typical manner of collection, which is usually suction of the desired fluid from above.

Figure 3C:
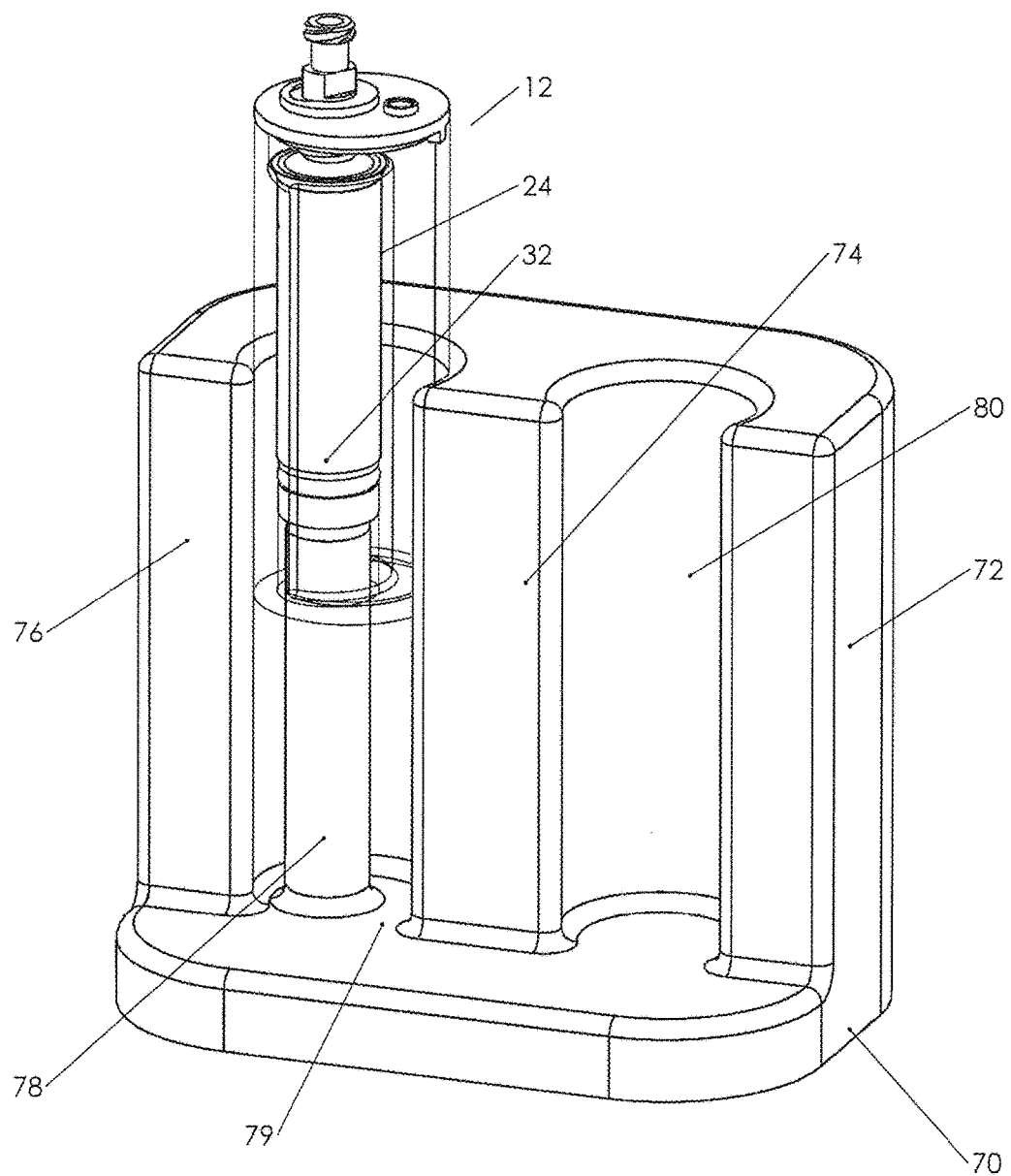
FIG. 3C is a cross-sectional perspective view of a holding device for use with Applicant's cup assembly.

FIG. 3C illustrates that a holding device 70 may be used with assembly 12 in two ways. First, holding device 70 may have walls 72/74, typically cylindrical, adapted to provide a receiving space 80 in which the outer container 14 may rest. Secondly, holding device 70 may have walls 74/76 configured to define an assembly/piston engaging space 79, which is configured with an upstanding piston engaging member 78, such that upon insertion of container in container assembly 12 into space 79, upstanding member 78 will engage the bottom of the piston when it is in the position as seen in FIG. 3A (post-centrifuge, but pre-pushout or spillover). It is seen with respect to FIG. 3C that pressing the assembly 12 downward using guide walls defining the side walls of space 79 will allow the user to observe the spillover, as well as the piston position so that the piston position may be stopped (the user stops inserting or pushing downward on cup 14) when the appropriate amount of spillover has been achieved and the piston is positioned properly (e.g., when the buffy coat or other selected fluid has a top surface just adjacent the rim defining open top 28). The user can then move assembly 12 into space 80, close plunger 46 to a closed position, and draw out the selected fluid.

Fluid concentration assembly 10 is seen in its basic form to include container-in-container assembly 12. It may also include container-in-container assembly 12 in addition to either holding device 70 or syringe (FIG. 3) or collection device (not shown) or any combination of the same.

FIGS. 4-10 illustrate a second example of a fluid concentration assembly 110. Functionally, the fluid concentration assembly is adapted to receive fluids, such as bone marrow concentrate or whole blood. It is further adapted to be insertable into a centrifuge machine so that, upon centrifuging, the fluid contents of the fluid concentration assembly separate, according to their densities. For example, blood will typically separate into a plasma, buffy coat, and a red blood cell portion, the red blood cell portion being more dense and therefore below the plasma which will reside on top of the red blood cell component in the fluid concentration assembly upon the completion of centrifuging. If bone marrow concentrate is in the fluid concentration assembly, it will typically centrifuge out into the plasma and red blood cell component, as well as a buffy coat between the two, which may contain undifferentiated cells or stem cells.

The health care professional will typically want to selectively remove one of the separated portions, for example, a red blood cell or buffy coat portion of a whole blood concentrate or a buffy coat portion of a bone marrow concentrate, or other biological fluid. It is a function of the biological fluid concentration assemblies in general to provide structure that may selectively remove one or more portions of the centrifuged separated fluids for later use.

Turning now to fluid concentration assembly 110, it is seen to provide some of the functions of the previous biological fluid concentration assemblies, albeit with structural differences and certain advantages gained thereby. The general structure of fluid concentration assembly 110 may be seen to be a container-in-container assembly 112, the assembly including an inner container 124 (shown here as a tube) configured for receipt and concentric placement within an outer container 114 (also shown here to be a tube), the two containers held in place by a base 122. Outer container 114 has a top outer perimeter 119 defining an open top 118. Inner container 124 is seen to have a bottom perimeter 126 defining an open bottom and a top perimeter 128 defining an open top. Outer container 114 has a bottom perimeter 120 defining an open bottom. The outer container 114 has walls 116. Inner container 124 has walls 125. The two containers have an annulus 123 therebetween, and base 122 is configured to be insertable into the bottom of the assembly, such that it seals the open bottoms of the two containers 114/124 in fixed fluid sealing relation as, for example, by gluing or heat.

Figure 4:
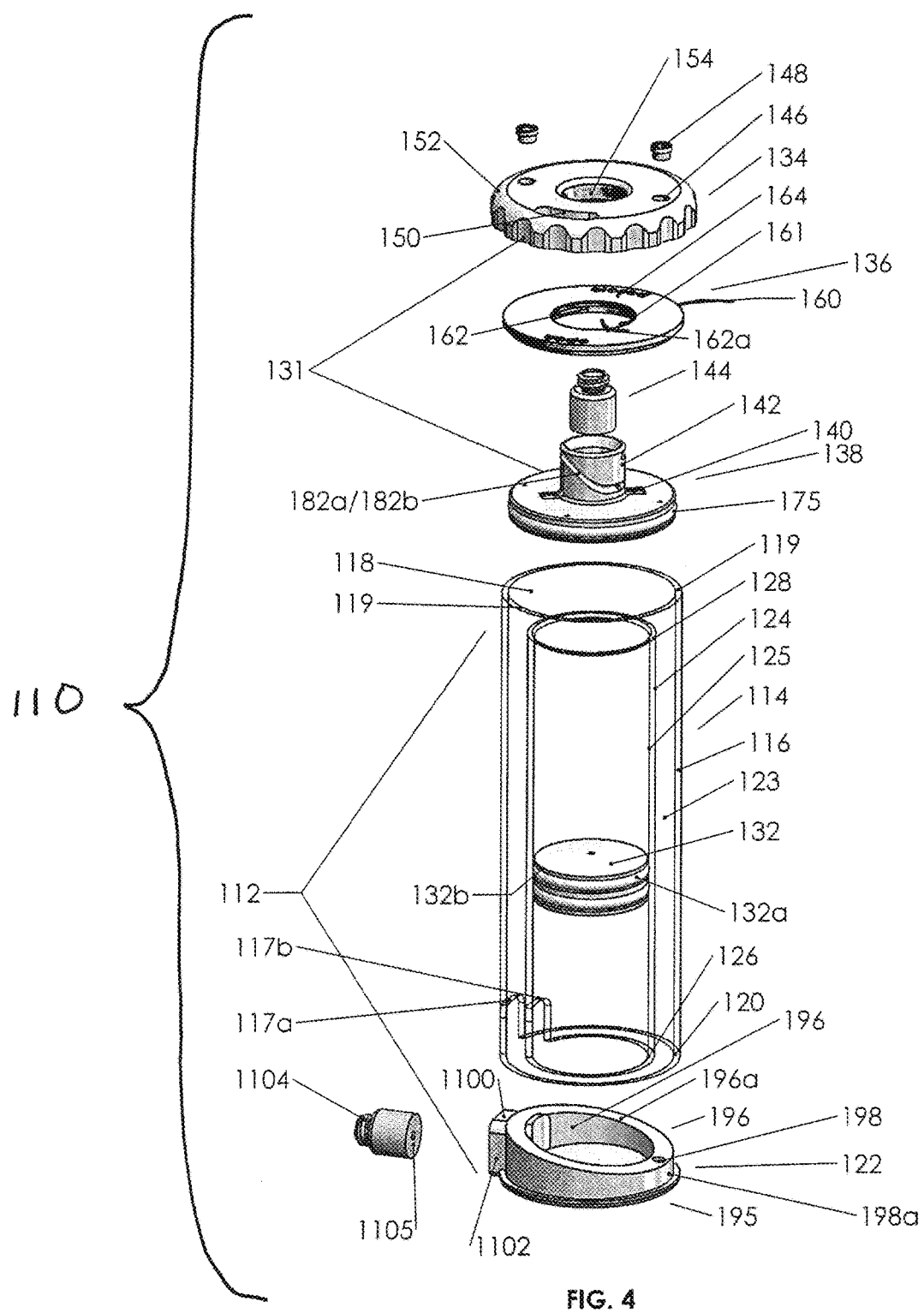
FIG. 4 is an exploded perspective view of another example biological fluid concentration assembly.

Apparent from FIG. 4 is that the bottom perimeters of the outer and inner containers are positioned laterally adjacent to one another, but the top perimeter 128 defining the open top of the inner tube 124 is located spaced apart and below the upper or top perimeter 119 of outer tube 114.

It is seen how base 122 seals annulus 123 (at the bottom) thereby creating a fluid chamber in the annulus, and it is seen how the base bottom wall 195 (see FIG. 4) also fluidly seals the open bottom of the inner container. Moreover, with reference to FIG. 4, it is seen that the base provides fluid communication in a channel through fluid device interface 1105 (e.g., a needle free valve, such as those available from Halkey Roberts Corp. of Saint Petersburg, Fla. (USA)), so that a drive fluid 127 (see FIG. 4A or 4B) may be driven through the fluid device interface into the inner tube or withdrawn from the inner tube through fluid device interface 1105. Fluid device interface 1105 may have a cap that will engage a threaded portion 1104, and may be used during the centrifuge stage of blood processing.

In FIGS. 4, 4A, and 4B, a piston 132 is configured to slideably and fluid sealingly engage inner wall 125 of inner container 124. Piston 132 may be cylindrical, as containers 114 and 124 are seen to be cylindrical and clear (see through), and piston 132 may have a walled surface with a multiplicity of grooves 132a therein, which grooves may be adapted to receive O-rings 132b or other sealing elements therein. It is seen that piston 132 seals a fluid volume above the O-rings defined by the inner walls of the inner container and a volume below the O-rings. A lid 136 is configured typically to be glued or otherwise made fluidly sealingly and integral with outer perimeter 119, so to be rigidly coupled thereto.

A plunger assembly 131 includes a cylindrical external cover 134 and a plunger 138. Plunger assembly 131 is adapted to engage the lid 136, and the external cover 134 is adapted to engage the plunger 138, such that rotation of external cover 134 moves the plunger along an axis perpendicular to the plane of rotation of the external cover, causing the plunger to move between an up or open position as seen in FIG. 4A and a down or closed position as seen in FIG. 4B. Moreover, with reference to FIGS. 4A and 4B, it will be seen that the open position allows fluid residing above piston 132 to spill over into an annulus 123 when piston 132 is forced upward as, for example, by action of a drive syringe 1112 (see FIG. 10) forcing the drive fluid below the piston upward against the underside of the piston.

Moreover, plunger assembly 131, more specifically, plunger 138, has a fluid device interface 144 (e.g., a needle free valve, such as those available from Halkey Roberts Corp. of Saint Petersburg, Fla. (USA)), engaged in a body or neck 142 thereof. Neck 142 is a cylindrical projection with a bore containing the fluid device interface, the fluid device interface containing a fluid channel 189 therethrough. Plunger 138 contains a cylindrical plunger base 140 configured to be slideably received within the outer container 114, the base having perimeter elastomeric sealing elements as set forth more specifically below. Neck 142 and plunger base 140, and possibly fluid device interface 144, are integral and define the plunger, which moves up and down as seen in FIGS. 4A and 4B, with rotation of the external cap 134 as more specifically set forth below. Plunger base 140 may have internal vents 141.

Figure 7:
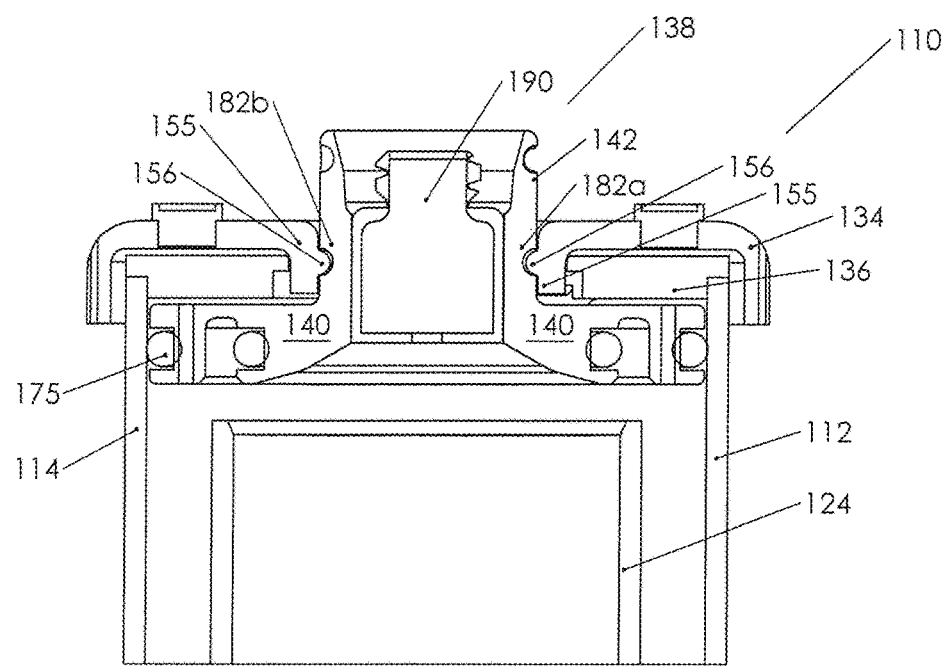
FIGS. 7, 7A, and 8 are closeup views in cross-section of the plunger assembly and lid of the second example concentration assembly, with FIG. 7 showing the manner in which the bosses of the inner walls of the external cap engage the drive tracks of the neck of the plunger, FIG. 7A showing the plunger in the closed position, and FIG. 8 showing the manner in which wedges on the outer surface of the inner walls of the cap engage an inwardly extending lip of the lid to capture the cap on the lid in such a fashion that the cap can rotate.
Figure 7A:
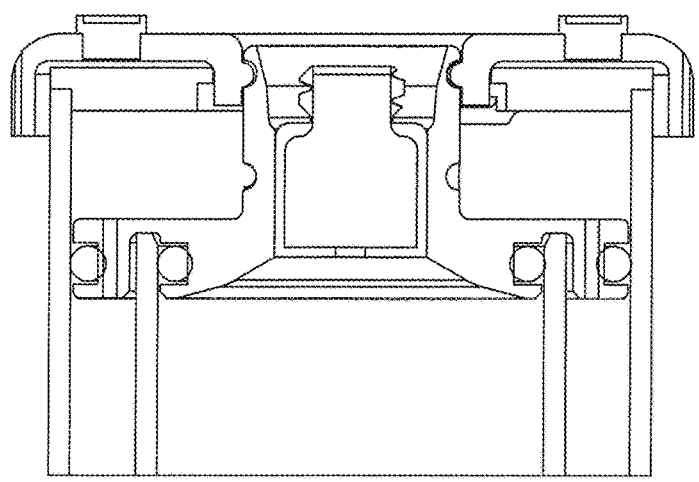

It is seen in FIGS. 4A, 4B, and 7, that the fluid device interface 144 with a channel 189 therethrough is positioned above the open top of the inner container 124. If a syringe 1110 (see FIG. 10) or other fluid bearing device is engaged to the fluid device interface 144, fluid may be forced through the fluid device interface and into the volume or space above the piston 132 in the inner container 124. One can also see that, if such a biological fluid were to be placed in the space above the piston and the plunger 138 were moved to the closed (or down) position (see FIG. 4B), centrifuging would generate separation of the biological fluid into its components. Subsequent opening of the plunger to the open (raised) position followed by pressurizing the drive fluid beneath the piston will cause an overflow, or a spillover, of the plasma or other less dense fluid residing on the top of the separated biological fluids as the piston is forced upward. The spillover will accumulate in annulus 123 between the inner and outer containers, and the operator may carefully observe the boundaries between the separated fluids. By careful observation and control of the pressure on a drive fluid syringe 1112 (see FIG. 10), the operator may position an upper layer of a selected fluid layer just adjacent top perimeter of the inner container, the plunger being in the open position. Subsequent to fluid positioning, rotation of the external cap can move the plunger to the closed position. Subsequent to closure, a collection syringe 1110 (see FIG. 10) or other fluid withdrawal device may be coupled to fluid device interface 144, and the selected fluid may be pushed up by the piston into syringe 1110.

Understanding the general function and structure of the plunger assembly 131, lid 136, and container-in-container assembly 112, Applicant notes more specific structure and related function as follows. External cap 134 may be seen to contain vents 146 with removable vent caps 148 disengaged therefrom. Vents 146 vent pressure differentials from above or below the cap, venting responsive to gas pressure differentials above and below the cap. The body of cap 134 is seen to have a window 150 therethrough. As cap 134 rests on top of fixed lid 136 and is rotatable therewith, window 150 provides viewing to indicia 164 on the upper surface of the lid, which indicia indicates with "closed" or "open," the position of the plunger (see FIG. 9).

Figure 8:
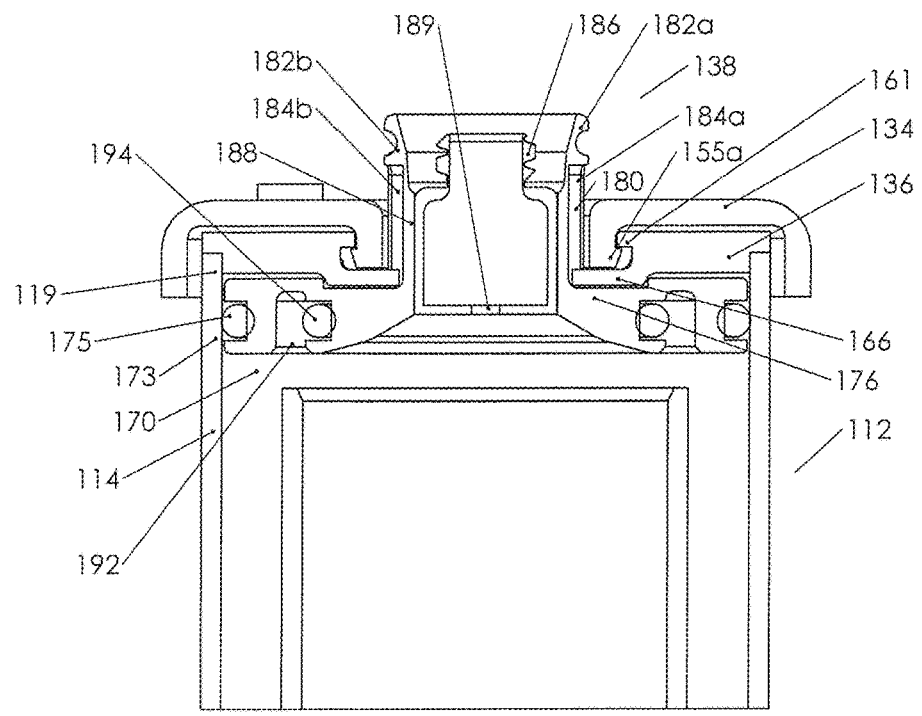

External cover or cap 134 is seen to have a ribbed outer rim 152, which is easily grasped, and an inner rim 154, which includes depending walls 155 defining a bore 154a. Walls 155 descend downward sufficiently to engage inner lip 161 of lid 136 (see FIG. 5), for example, by resilient wedge elements 155a on the outer surfaces of walls 155 (see FIG. 5). Thus, external cap 134 is seen to be rotatably "captured" on lid 136 with outer rim 152 depending downward over the walls defining the top or upper perimeter 119 of the outer container as best seen in FIG. 8.

With further reference to lid 136 in FIGS. 5 and 7, it may be seen that inwardly projecting plunger drive bosses 156, typically two opposed on the inner walls of depending walls 155, are present and are adapted to engage neck 142 of plunger 138 as more further set forth below so as to drive plunger 138 vertically up and down (by virtue of rotation of cap 134), without rotating the plunger.

Turning now to lid 136, it is seen to include notched outer rim 160 for secure engagement with top perimeter 119 and an inner lip 161 for engaging external cap 134 as set forth above. Moreover, inner walls 162 of which the inner lip is part thereof, define a bore 162a adapted to receive neck 142 therethrough, and neck 142 also is adapted to pass through bore 154a of cover 134. Indicia 164 may be found on the top surface of lid 136. Lid 136 includes anti-rotation tabs 166, which are affixed to the lower surface of the lid and project both downward from the lower surface thereof and inward into bore 162a in the illustrated embodiment. The anti-rotation tabs are adapted to engage neck 142 of plunger 138, so as to prevent plunger 138 from rotating responsive to rotation of external cap 134 (and thereby for forcing the plunger to move downward without rotation.)

Figure 5:
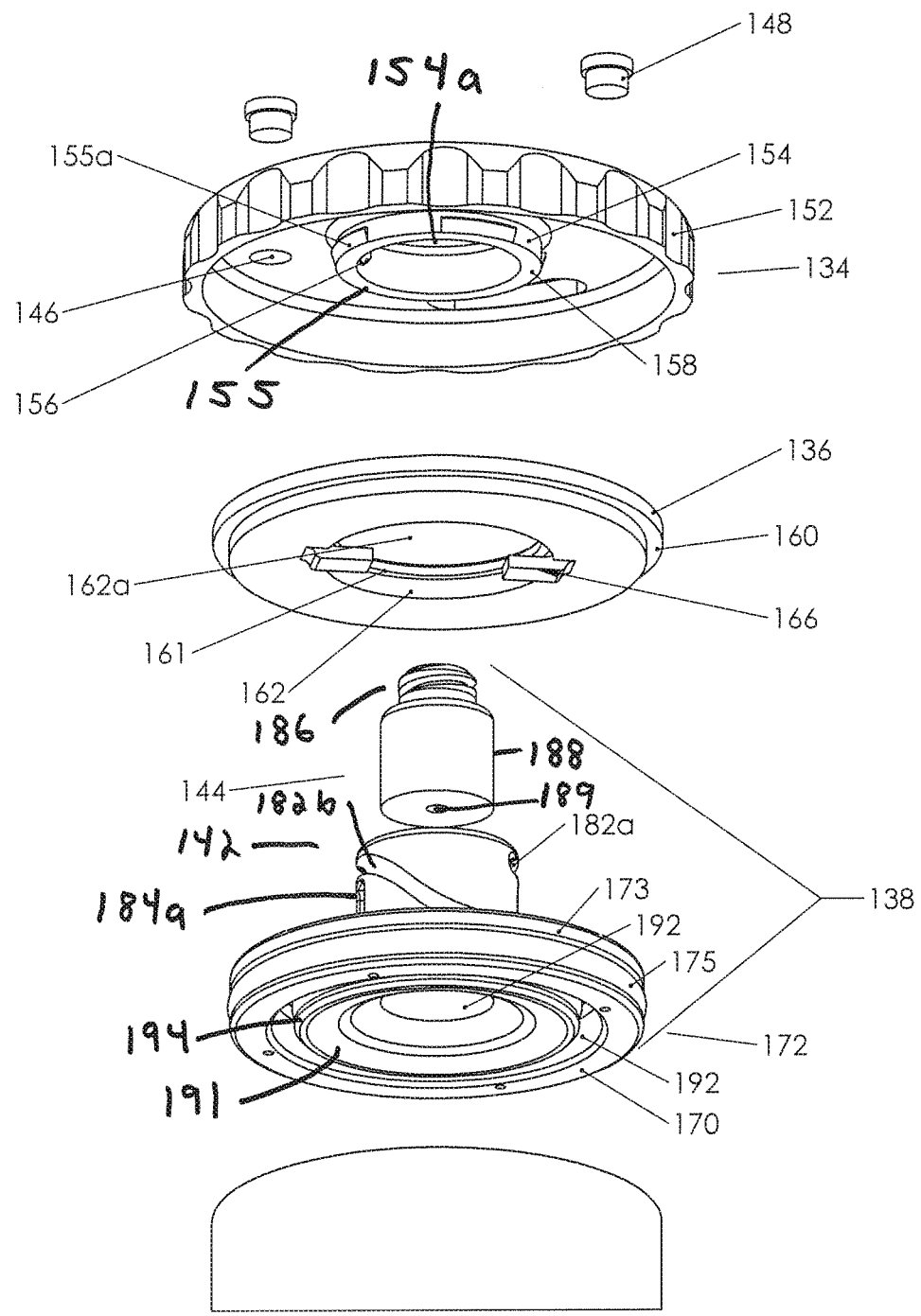
FIGS. 5 and 6 are perspective exploded detail views of the plunger assembly and lid of the second example biological fluid concentration assembly.
Figure 6:
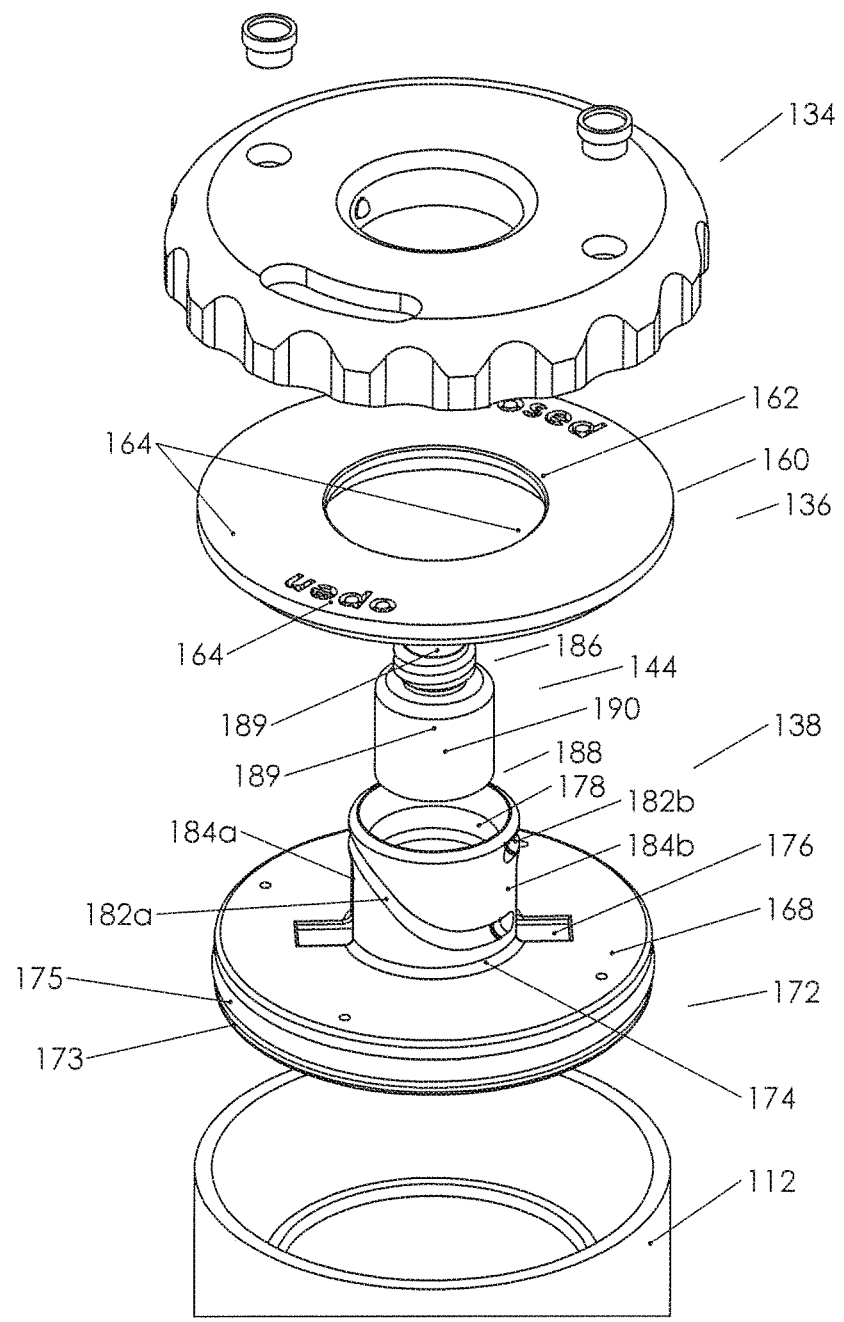

Turning now to plunger base 140 and as seen in FIGS. 5 and 6, it is integral with neck 142 and generally cylindrical, having an upper surface 168 and a lower surface 170. An outer rim 172 may contain a groove 173 for receipt of an elastomeric sealing element 175 (e.g., an O-ring) therein, the base having a diameter such that the outer rim fits snugly against the inner walls of the outer container 114 as seen, for example, in FIGS. 7 and 8. The neck and base are integral at neck joinder walls or area 174, and the upper surface 168 of plunger base 140 is seen to have a pair of pockets 176, which are dimensioned and located such that when the upper surface of the base is flush against the lower surface of the lid, anti-rotation tabs 166 on the lower surface of the lid fit into pockets 176, allowing a full up or open position of the plunger as best seen in FIG. 8. Pockets 176 may also assist with resisting rotation of plunger 138.

Lower surface 170 of plunger base 140 is seen to contain a circular recess 192 defining an inner rim 191 with a groove for a sealing element 194 (e.g., an O-ring) on the walls of the inner rim, which circular recess and inner rim 191 is positioned such that in a down, or closed, position as best seen in FIG. 4B, the sealing element located on the inner rim 191, seals against the inner walls of the inner tube just beneath the open end or open top of the inner tube.

Figure 9:
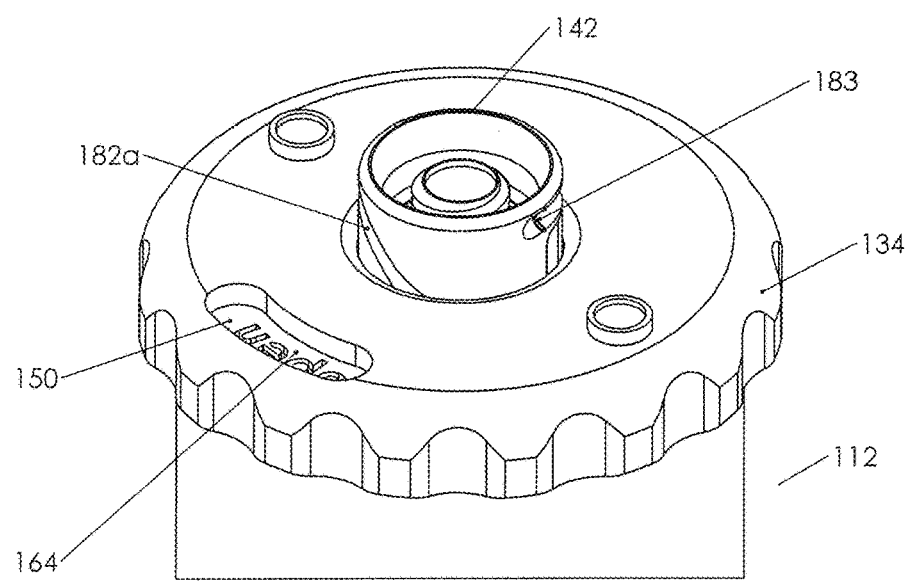
FIG. 9 is a perspective view showing the upper surface of the cap on the lid, showing a locking snap ridge protruding from the end of the ridge to prevent unintentional twisting.

Turning now to the neck 142 of plunger 138 and as best seen in FIGS. 5 and 7, it is seen to extend vertically upward from the upper surface of plunger base 140. Neck 142 includes inner walls 178 defining a bore, which receives fluid device interface 144 fixedly and rigidly therein. Outer walls 180 of neck 142 are seen to include a pair of curved cam grooves or drive tracks 182a/182b and a pair of vertical anti-rotation slots 184a/184b. Drive tracks 182a/182b are configured to each receive one boss 156 snugly therein, and anti-rotation slots 184*a*/184*b* (see FIG. 8) each will accept the inwardly extended portions of the anti-rotation tabs 166 thereinto. Rotation of external cover or cap 134 drives the neck and, therefore, the plunger 138 vertically as anti-rotation tabs 166 in the anti-rotation slots 184*a*/184*b* prevent the plunger from rotating with the cap (and therefore going nowhere in the vertical dimension). Drive tracks 182*a*/182*b* being, in part, curved as they are and the vertical vector of the forces between the bosses and the drive tracks generating vertical motion, any rotational motion of the plunger is prevented by the engagement of the lid 136 with anti-rotation tabs/slots 184*a*/184*b*. Thus, it is seen how rotation of the external cap 134 can move the plunger between an open and closed position, the open position allowing spill-over and the closed position sealing the inner container. In both positions, and in between, the plunger seals against the inner walls of outer container 114 (see FIGS. 4A and 4B). FIG. 9 also illustrates a protruding detent 183 (e.g., a ridge) at the upper end of each of drive tracks 182*a*/182*b* to provide a snap fit for resiliently engaging the boss to help prevent inadvertent rotation of the cap when the plunger is in the closed position. A detent could also be placed at the bottom of the drive tracks to snap the cap into place when the plunger is in the open position.

Fluid device interface 144 is adapted to receive a syringe on a collection syringe engagement portion 186 thereof. Outer walls 188 of fluid device interface 144 are designed to fit snugly and to be glued or otherwise affixed into the bore of neck 142. In certain implementations, fluid channel 189 in the fluid device interface may have a sealing foam 190 therein, which sealing foam is responsive to a pressure differential across the removed surfaces thereof so as to, in a neutral pressure condition, prevent fluid from passing therethrough and, in a fluid pressure differential situation, either greater pressure below or above the fluid device interface, to allow fluid to flow therethrough. The structure and function of fluid-pressure-responsive fluid device interfaces show them to be medical valves in the nature of substitutes for needle ports, and provide one or two way fluid communication across a pressure differential (see website at domain name "halkeyroberts.com").

Figure 10:
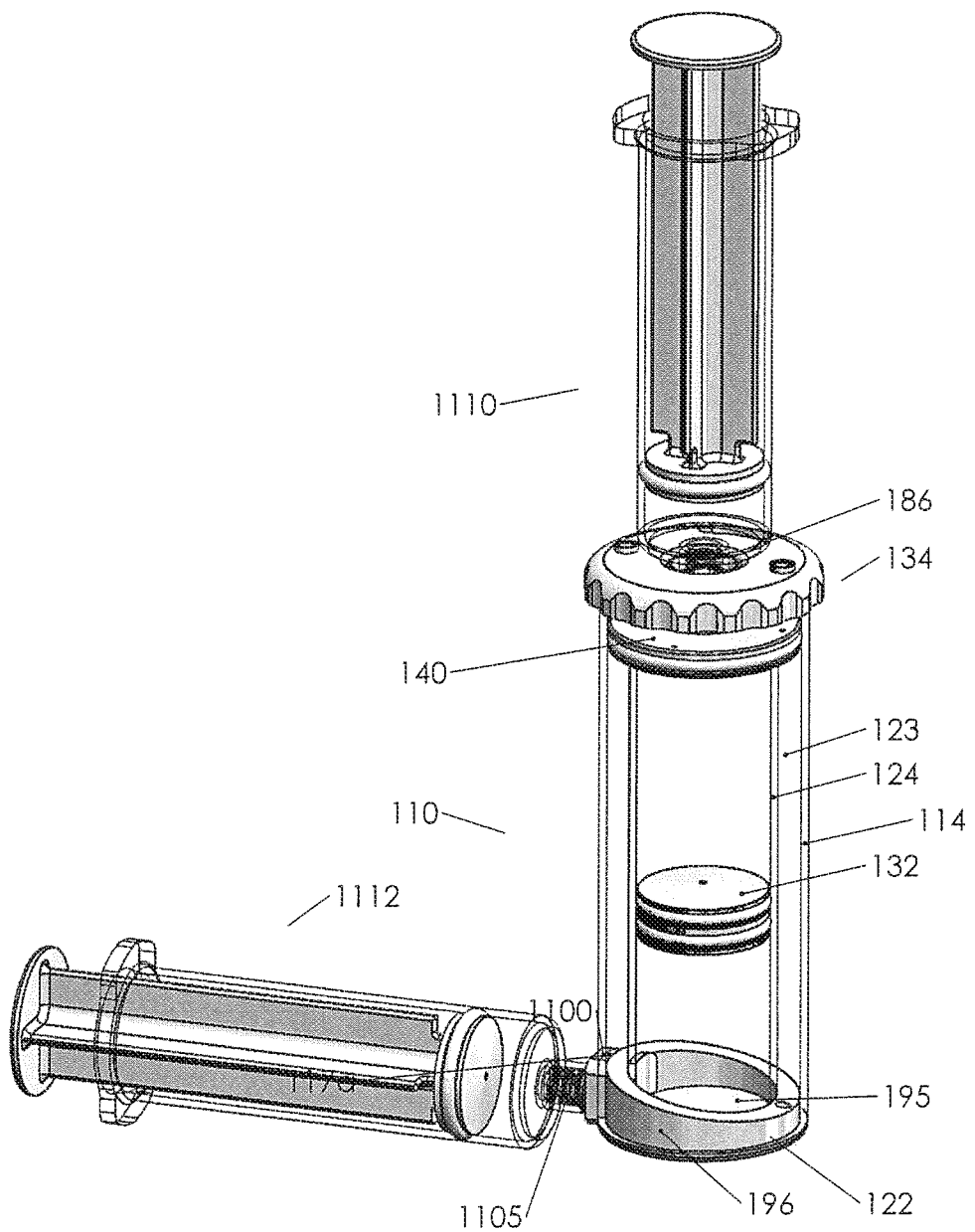
FIG. 10 is a perspective view of the second example fluid concentration assembly showing the manner in which a piston drive syringe is used for engagement with a base, as well as a manner in which a biological fluids cylinder is engaged with the fluid device interface and the neck of the plunger.

Turning to FIGS. 4 and 10, it may be seen that base 122 is configured to seal off annulus 123 and the bottom of inner container 124, while also providing fluid communication from outside the base and into the inner container, such that coupling a drive syringe 1112 to base 122 allows the user to force a gas or other fluid into the inner container below piston 132 and push the piston upward or to withdraw fluid and allow piston 132 to drop and, therefore, selectively control the position of fluids in the inner tube, including separated fluids.

Bottom wall 195 of base 122 fluid sealingly engages the bottom of inner container 124. Upstanding wall 196 fits within the annulus 123 and may have a top surface 196*a* that is tilted toward a rescue vent 198. Rescue vent 198 passes through wall 196 from top through bottom and connects to annulus 123 through a silicon bead or other piercable fluid stop 198*a* in the rescue vent. In this manner, rescue vent 198 may be punctured with a needle or syringe coming from beneath and up into the annulus so as to withdraw or "rescue" a fluid that was inadvertently spilled over or pushed over the top of the inner tube.

Part of the body of base 122 includes a notch 1100 configured to be received in cutouts 117*a* and 117*b* located at the bottom of the outer and the inner containers. A horizontal channel 1102 through the base 122 is adapted to accept fluid device interface 1105 fluidly sealed therein. Threaded portion 1104 of the fluid deivce interface is adapted to receive syringe 1112 or other fluid containing device (see FIG. 10).

FIG. 10 illustrates a manner in which biological concentration assembly 110 may engage a biological fluids transfer syringe 1110 and piston drive syringe 1112. Biological fluids transfer syringe 1110 has an end for threaded engagement to the threads of syringe engagement portion 186 of fluid device interface 144 for fluid tight coupling therewith. Syringe 1110 may carry an undifferentiated blood or biological fluid specimen to collection assembly 110, and threaded to the neck of the plunger, this fluid may be transferred into the portion of the inner container above the piston. Piston fluid drive syringe 1112 may be filled with a saline solution or other suitable fluid injectable into the inner container in the space below the piston to advance (drive) the piston or extract the fluid from the inner container to retract the piston responsive to movement of the plunger of drive syringe 1112. Either an incompressible fluid (e.g., a liquid) or a compressible fluid such as a gas (e.g., air), may be used to advance and/or retract the piston. Following centrifugation, for example, syringe 1112, with syringe 1110 secured, can be used to urge piston 132 upward so as to drive a differentiated fluid either into the annulus via spillover (plunger up) or, with a selected fluid adjacent the top of the inner container and the plunger in the down or closed position, advancing the piston upward to drive a selected fluid into syringe 1110.

Although the inventive concepts have been described with reference to example embodiments, this description is not meant to be construed in a limiting sense. On the contrary, various modifications of the disclosed embodiments will be readily apparent to those skilled in the art upon reference to the description of the invention. Moreover, various features of each embodiment may be used with the other. For example, the plunger assembly of assembly 10 may be used with assembly 110, and the plunger assembly of assembly 110 may be used with assembly 10. As another example, the piston drives are interchangeable. As a further example, a scale similar to the one for assembly 10 may be used with assembly 110. It is therefore contemplated that the appended claims will cover such modifications, alternatives, and equivalents that fall within the true spirit and scope of the invention.

The invention claimed is:
1. A biological fluids concentration assembly, comprising:
 a tube in tube assembly defining a vertical axis and comprising a cylindrical outer tube and a cylindrical inner tube, the inner tube having a smaller diameter, with an annulus between the two tubes, both tubes having open tops and bottoms, the open top of the inner tube being located below the open top of the outer tube, and a base engaging the outer tube and the inner tube at the bottom ends and a floor for engaging the open bottom of the inner tube thereof, the base with a channel for allowing fluid communication between the exterior of the tube in tube assembly and the interior of the inner tube;
 a piston for slidably and fluid sealingly engaging the inner walls of the inner tube above the base and below the top of the inner tube;
 a lid for engaging to the open top of the outer tube, the lid having a central bore and anti-rotation tabs, and
 a plunger assembly comprising a plunger, a cap with inner rim walls defining a central bore, the inner rim walls having projecting drive bosses, the cap with walls for rotatable engagement with the lid and the plunger, the plunger having a base having an upper and lower surface and a neck, the plunger having a fluid channel therethrough, the neck having a track, wherein the track engages the projecting drive bosses of the cap and wherein the anti-rotation tabs of the lid engage the plunger such that rotation of the cap moves the plunger longitudinally without rotating the plunger, the cap moving between an open position wherein the lower surface of the base is off the open top of the inner tube and a closed position, wherein the lower surface of the base engages the open top of the inner tube so as to fluidly seal the open top.

2. The assembly of claim 1, wherein the assembly base includes an external port, the port engaged with the channel, the port including walls dimensioned to receive and fluidly couple with a device thereon for injecting and withdrawing a drive fluid into and out of the inner tube below the piston, such that the piston moves up and down in the inner tube responsive to such action.

3. The assembly of claim 1, wherein the anti-rotation tabs of the lid engage anti-rotation slots of the neck.

4. The assembly of claim 1, wherein the cap includes members for holding the cap to the outer tube while allowing the cap to rotate with respect to the tube.

5. The assembly of claim 4, wherein the lid includes a perimeter lip on the walls adjacent the central bore and wherein the cap members for holding includes resilient wedge elements for coupling with the perimeter lip of the central bore of the lid.

6. The assembly of claim 1, wherein the base of the plunger includes perimeter walls for fluid sealingly engaging the top of the inner tube when the plunger is in the dosed position.

7. The assembly of claim 6, wherein the base of the plunger also includes a perimeter adjacent the inner walls of the outer cylinder to fluid sealing engage the same.

8. The assembly of claim 1, wherein the plunger includes a needle free valve engaging the fluid channel such that fluid passing through the plunger passes through the needle free valve.

9. The assembly of claim 1, wherein the base of the tube-in-tube assembly includes a rescue vent.

10. The assembly of claim 1, wherein the channel of the base of the tube-in-tube assembly includes a needle free valve.

11. The assembly of claim 1, wherein the piston has a solid body with a top surface, a bottom surface, and a perimeter and includes an O-ring adapted to fluidly seal the body of the piston to the inner walls of the inner tube.

12. The assembly of claim 1, wherein the annulus is adapted to receive a portion of a biological fluid that may spill over the top of the inner tube when the piston is moved towards the lid.

* * * * *